United States Patent [19]

Kato et al.

[11] Patent Number: 4,501,756
[45] Date of Patent: Feb. 26, 1985

[54] FUNGICIDAL CARBAMATES USEFUL AGAINST FUNGI RESISTANT TO BENZAMIDAZOLE FUNGICIDES

[75] Inventors: Toshiro Kato; Junya Takahashi, both of Hyogo; Katsuzo Kamoshita, Osaka, all of Japan

[73] Assignee: Sumitomo Chemical Company, Limited, Osaka, Japan

[21] Appl. No.: 315,860

[22] Filed: Oct. 28, 1981

[30] Foreign Application Priority Data

Nov. 7, 1980 [JP] Japan .................. 55-157237
Nov. 27, 1980 [JP] Japan .................. 55-167684
Feb. 13, 1981 [JP] Japan .................. 56-20534

[51] Int. Cl.³ .............. A01N 47/20; A01N 43/36; A01N 43/50; A01N 43/52; A01N 57/30
[52] U.S. Cl. .................. 514/120; 560/24; 560/29; 560/30; 514/376; 514/391; 514/397; 514/398; 514/421; 514/479
[58] Field of Search .................. 560/24, 29, 30; 424/300, 215, 272, 273 B, 273 R, 274

[56] References Cited

U.S. PATENT DOCUMENTS 2,537,691  1/1951  Mowry et al. .................. 424/300
2,946,768  7/1960  Klauke et al. .................. 260/453 P

FOREIGN PATENT DOCUMENTS 43-107    1/1968  Japan .
43-24065 10/1968  Japan .
44-29276 11/1969  Japan .

OTHER PUBLICATIONS

Fujinami et al, *Agricultural Biological Chemistry*, vol. 35, pp. 1707–1719 (1971).
Hackh's Chemical Dictionary, Fourth Edition, McGraw-Hill, Publ. (1969) p. 677.
Takematsu, Tetsuo et al., Chemical Abstracts, vol. 71 (1969) #29,515y.
Mukai, Toshihiko et al., Chemical Abstracts, vol. 87 (1977) #52,961e.
Siegel et al, "Antifungal Compounds", vol. 2, pp. 107–112.
Pommer et al, "Crop Protection", vol. 1, pp. 221–230 (1982).
Chemical Abstracts, vol. 25, No. 8, Apr. 20, 1931 p. 1816.

*Primary Examiner*—Natalie Trousof
*Assistant Examiner*—L. Hendriksen
*Attorney, Agent, or Firm*—Birch, Stewart, Kolasch & Birch

[57] ABSTRACT

Use of a compound of the formula:

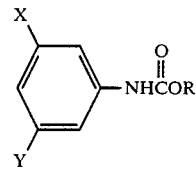

wherein X and Y are, same or different, each a lower alkyl group, a lower alkoxy group or a halogen atom and R is a methyl group or an ethyl group as a fungicidal agent against plantpathogenic fungi, particularly their drug-resistant strains.

10 Claims, No Drawings

FUNGICIDAL CARBAMATES USEFUL AGAINST FUNGI RESISTANT TO BENZAMIDAZOLE FUNGICIDES

The present invention relates to fungicides. More particularly, it relates to a fungicidal composition comprising an N-phenylcarbamate of the formula:

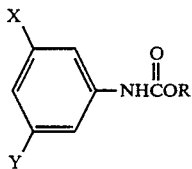
(I)

wherein X and Y, which are the same or different, are each a lower alkyl group, a lower alkoxy group or a halogen atom and R is a methyl group or an ethyl group and an inert carrier, and a method of controlling fungi. It also pertains to a novel fungicidal N-phenylcarbamate of the formula:

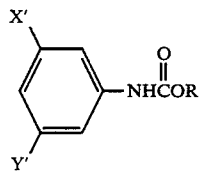
(I')

wherein X' is a lower alkyl group, a lower alkoxy group, a chlorine atoms, a fluorine atom, a bromine atom or an iodine atom, Y' is a lower alkyl group, a lower alkoxy group, a fluorine atom, a bromine atom or an iodine atom and R is a methyl group or an ethyl group, and to a process for production thereof.

It has been known that benzimidazole fungicides including thiophanate such as Benomyl(methyl 1-(butylcarbamoyl)benzimidazol-2-ylcarbamate), Fubelidazol(2-(2-furyl)benzimidazole), Thiabendazole(2-(4-thiazolyl)benzimidazole), Carbendazim(-methyl benzimidazol-2-ylcarbamate), Thiophanatemethyl(1,2-bis(3-methoxycarbonyl-2-thioureido)benzene), Thiophanate(1,2-bis(3-ethoxycarbonyl-2-thioureido)-benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene show an excellent fungicidal activity against various plant pathogenic fungi and that they have been widely used as agricultural fungicides since 1970. It has also been known, however, that their continuous application over a long period of time provides phytopathogenic fungi with tolerance to them, whereby their plant disease-preventive effect is much lowered. Further, the fungi which gained tolerance to certain kinds of benzimidazole thiophanate fungicides also show considerable tolerance to some other kinds of benzimidazole thiophanate fungicides. Thus, they are apt to obtain cross-tolerance. Therefore, if any material decrease of their plant disease-preventive effect in certain fields is observed, their application to such fields has to be discontinued. But, it is often observed that the density of drug-resistant organisms is not decreased even long after the discontinuation of the application. Although other kinds of fungicides have to be employed in such a case, only few are so effective as benzimidazole thiophanate fungicides in controlling various phytopathogenic fungi. Dicarboximide fungicides such as Promidone(3-(3',5'-dichlorophenyl)-1,2-dimethylcyclopropane-1,2-dicarboximide), Iprodione(3-(3',5'-dichlorophenyl)-1-isopropylcarbamoylimidazolidine-2,4-dione), Vinchlozoline(3-(3',5'-dichlorophenyl)-5-methyl-5-vinyloxazoline-2,4-dione), ethyl(RS)-3-(3',5'-dichlorophenyl)-5-methyl-2,4-dioxooxazolidine-5-carboxylate, etc., which are effective against various plant diseases, particularly those caused by *Botrytis cinerea*, have the same defects as previously explained with respect to the benzimidazole thiophanate fungicides.

In Agricultural Biological Chemistry, Vol. 35, pages 1707–1719 (1971), it is described that methyl N-(3,5-dichlorophenyl)carbamate and ethyl N-(3,5-dichlorophenyl)-carbamate were tested for determination of their antibiotic potency against *Sclerotinia sclerotiorum* according to the agar dilution method but showed only an extremely weak potency in comparison with other structurally related compounds such as α-cyanoisopropyl N-(3,5-dichlorophenyl)-carbamate and α-ethoxycarbonylisopropyl N-(3,5-dichlorophenyl)carbamate.

On the other hand, C. R. Acad. Sc. Paris, t. 289, S'erie D, pages 691–693 (1979) reports that such herbicides as Barban(4-chloro-2-butynyl N-(3-chlorophenyl)carbamate)), Chlorobufam(1-methyl-2-propynyl N-(3-chlorophenyl)carbamate), Chlorpropham(isopropyl N-(3-chlorophenyl)carbamate) and Propham(isopropyl N-phenylcarbamate) exhibit a fungicidal activity against certain organisms tolerable to some of benzimidazole thiophanate fungicides. As readily understood from their herbicidal use, however, their foliar application to crop plants as fungicides causes serious chemical injury thereon. In addition, their fungicidal activity against the drug-resistant fungi is not strong enough and hence they can not be used as a fungicide.

As a result of a study, it has now been found that N-phenylcarbamates of the formula:

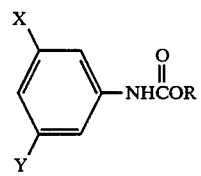
(I)

wherein X and Y are, same or different, each a lower alkyl group (e.g. methyl, ethyl, propyl, butyl, pentyl, hexyl, heptyl, octyl), a lower alkoxy group (e.g. methoxy, ethoxy, propoxy, butoxy, pentyloxy, hexyloxy, heptyloxy, octyloxy) or a halogen atom (e.g. chlorine, bromine, iodine, fluorine) and R is a methyl group or an ethyl group show an excellent fungicidal activity against plant pathogenic fungi which have developed resistance to the benzimidazole thiophanate fungicides and/or the cyclic imide fungicides. It is notable that their fungicidal potency against the organisms tolerant to the benzimidazole thiophanate fungicides and/or the cyclic imide fungicides (hereinafter referred to as "drug-resistant strains") is much higher than that against the organisms sensitive to the benzimidazole thiophanate fungicides and/or the cyclic imide fungicides (hereinafter referred to as "drug-sensitive strains").

Thus, the present invention provides a fungicidal composition comprising as an active ingredient a fungicidally effective amount of an N-phenylcarbamate of the formula:

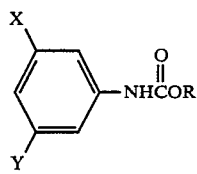

(I)

wherein X and Y are, same or different, each a lower alkyl group, a lower alkoxy group or a halogen atom and R is a methyl group or an ethyl group, and an inert carrier, which composition is fungicidally effective, especially against the plant pathogenic fungi which developed resistance to the benzimidazole thiophanate fungicides and/or the cyclic imide fungicides.

It also provides a novel, fungicidal compound of the formula:

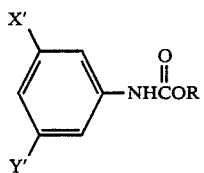

(I')

wherein X' is a lower alkyl group, a lower alkoxy group, a chlorine atom, a fluorine atom, a bromine atom or an iodine atom, Y' is a lower alkyl group, a lower alkoxy group, a fluorine atom, a bromine atom or an iodine atom and R is as defined above, and a process for production thereof.

It provides a method of controlling plant pathogenic fungi including those which developed resistance to the benzimidazole thiophanate fungicides and/or the cyclic imide fungicides. The present invention further provides a combination composition comprising as an active ingredient the N-phenylcarbamates of the formula (I) in combination with a benzimidazole thiophanate fungicide and/or a cyclic imide fungicide, which composition is fungicidally effective against not only drug-sensitive but also drug-resistant fungi, and which is effective for the prevention of plant diseases.

Examples of the benzimidazole thiophanate fungicides are Benomyl(methyl 1-(butylcarbamoyl)benzimidazol-2-ylcarbamate), Fubelidazol(2-(2-furyl)benzimidazole), Thiabendazole(2-(4-thiazolyl)benzimidazole), Carbendazim(methyl benzimidazol-2-ylcarbamate), Thiophanate-methyl(1,2-bis(3-methoxycarbonyl-2-thioureido)benzene), Thiophanate(1,2-bis(3-ethoxycarbonyl-2-thioureido)benzene), 2-(O,S-dimethylphosphorylamino)-1-(3'-methoxycarbonyl-2'-thioureido)benzene, 2-(O,O-dimethylthiophosphorylamino)-1-(3'-methoxycarbonyl-2'-thioureido)benzene, etc. Examples of the cyclic imide fungicides are procymidone(3-(3',5'-dichlorophenyl)-1,2-dimethylcyclopropane-1,2-dicarboximide), Iprodione(3-(3',5'-dichlorophenyl)-1-isopropylcarbamoylimidazolidine-2,4-dione), Vinchlozoline(3-(3',5'-dichlorophenyl))-5-methyl-5-vinyloxazolidine-2,4-dione), ethyl(RS)-3-(3',5'-dichlorophenyl)-5-methyl-2,4-dioxooxazolidine-5-carboxylate, etc.

Among the N-phenylcarbamates (I), those wherein both of X and Y are chlorine are known, and others are novel. Thus, the N-phenylcarbamates of the formula (I) wherein X is lower alkyl, lower alkoxy, chlorine, fluorine, bromine or iodine, Y is lower alkyl, lower alkoxy, fluorine, bromine or iodine and R is methyl or ethyl are novel.

The compositions of the invention are fungicidally effective against a wide scope of plant pathogenic fungi, of which examples are as follows: *Podosphaera leucotricha, Venturia inaequalis, Mycosphaerella pomi, Marssonina mali* and *Sclerotinia mali* of apple, *Phyllactinia kakicola* and *Gloeosporium kaki* of persimmon, *Cladosporium carpophilum* and *Phomopsis* sp. of peach, *Cercospora viticola, Uncinula necator, Elsinoe ampelina* and *Glomerella cingulata* of grape, *Cercospora beticola* of sugar beet, *Cercospora arachidicola* and *Cercospora personata* of peanut, *Erysiphe graminis* f. sp. *hordei, Cercosporella herpotrichoides* and *Fusarium nivale* of barley, *Erysiphe graminis* f. sp. *tritici* of wheat, *Sphaerotheca fuliginea* and *Cladosporium cucumerinum* of cucumber, *Cladosporium fulvum* of tomato, *Corynespora melongenae* of eggplant, *Sphaerotheca humuli, Fusarium oxysporum* f. sp. *fragariae* of strawberry, *Botrytis alli* of onion, *Cercospora apii* of celery, *Phaeoisariopsis griseola* of kidney bean, *Erysiphe cichoracearum* of tobacco, *Diplocarpon rosae* of rose, *Elsinoe fawcetti, Penicillium italicum, Penicillium digitatum* of orange, *Botrytis cinerea* of cucumber, eggplant, tomato, strawberry, pimiento, onion, lettuce, grape, orange, cyclamen, rose or hop, *Sclerotinia sclerotiorum* of cucumber, eggplant, pimiento, lettuce, celery, kidney bean, soybean, azuki bean, potato or sunflower, *Sclerotinia cinerea* of peach or cherry, *Mycosphaerella melonis* of cucumber or melon, etc. Namely, the composition of the invention is highly effective in controlling the drug-resistant strains of the said fungi. Advantageously, it has extremely low toxicity and has little detrimental actions on mammals and fish. Also, it may be applied to the agricultural field without causing any material toxicity to important crop plants.

The N-phenylcarbamates compound (I) can be prepared by either one of the following procedures:

(a) Reacting an aniline of the formula:

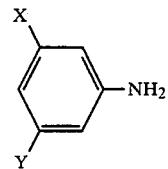

(II)

wherein X and Y are each as defined above with methyl chloroformate or ethyl chloroformate.

The reaction is usually carried out in the presence of an inert solvent (e.g. benzene, toluene, xylene, diethyl ether, tetrahydrofuran, dioxane, chloroform, carbon tetrachloride, ethyl acetate, pyridine, dimethylformamide). When desired, the reaction may be performed in the existence of a dehydrohalogenating agent (e.g. pyridine, triethylamine, diethylaniline, sodium hydroxide, potassium hydroxide) so as to obtain the objective compound (I) in a high yield. The reaction may be accomplished at a temperature of 0° to 150° C. instantaneously or within 10 hours.

The aniline (II) used as the starting material in the above procedure can be prepared according to the methods as described in Yakugaku Zasshi, 85, 314–317 (1965) and Ber., 34, 3343–3354 (1901).

(b) Reacting a phenyl isocyanate of the formula:

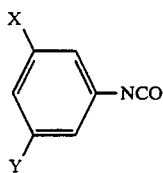

(III)

wherein X and Y are each as defined above with methanol or ethanol.

The reaction is usually carried out in the absence or presence of an inert solvent (e.g. benzene, toluene, xylene, diethyl ether, tetrahydrofuran, dioxane, N,N-dimethylformamide, chloroform, carbon tetrachloride). When desired, a catalyst (e.g. triethylamine, diethylaniline, 1,4-diazabicyclo(2,2,2)octane) may be used. The reaction is normally accomplished at a temperature of 0° to 50° C. instantaneously or within 10 hours.

The phenyl isocyanate (III) used as the starting material in the above procedure can be prepared by reacting the aniline (II) with phosgene. This reaction is usually carried out in the presence of an inert solvent (e.g. benzene, toluene, xylene, ethyl acetate) at a temperature of 50° C. to the refluxing temperature of the solvent. The reaction may be accomplished instantaneously or within 10 hours.

Some embodiments of the procedures for preparation of the N-phenylcarbamate (I) are illustratively shown in the following Examples.

EXAMPLE 1

Synthesis of ethyl N-(3,5-diisopropyloxyphenyl)-carbamate (Compound No. 16) (according to Procedure (a)):

3,5-Diisopropyloxyaniline (2 g) and diethylaniline (1.5 g) were dissolved in benzene (20 ml). To the resultant mixture was dropwise added ethyl chloroformate (1.2 g) under ice-cooling. After being allowed to stand at room temperature for 12 hours, the reaction mixture was poured into ice water and extracted with ethyl acetate. The extract was washed with water, dried over magnesium sulfate, and concentrated under reduced pressure. The residue was purified by silica gel chromatography using a mixture of benzene and tetrahydrofuran as the eluent to give ethyl N-(3,5-diisopropyloxyphenyl)carbamate (1.9 g) in a yield of 67.6%. M.P., 81.5°–82° C.

Elementary analysis: Calcd. for $C_{15}H_{23}NO_4$: N, 4.98%; C, 64.03%; H, 8.24%. Found: N, 4.93%; C, 63.99%; H, 8.32%.

EXAMPLE 2

Synthesis of methyl N-(3,5-dimethoxyphenyl)-carbamate (Compound No. 11) (according to Procedure (b)):

A mixture of 3,5-dimethoxyaniline (8.4 g) in toluene (100 ml) was dropwise added to a toluene solution containing 20 g of phosgene at 10° to 20° C. The resulting mixture was gradually heated and, after being refluxed for 30 minutes, cooled to room temperature. The solvent was removed by distillation under reduced pressure to give (3,5-dimethoxy)phenyl isocyanate (9.8 g). The thus obtained crude substance was added to a methanol solution (50 ml) containing triethylamine (1 g). The resultant mixture was allowed to stand at room temperature for 12 hours, poured into ice-water and extracted with ethyl acetate. The extract was washed with water, dried over magnesium sulfate and concentrated under reduced pressure. The residue was purified by silica gel chromatography using a mixture of benzene and tetrahydrofuran as the eluent to give methyl N-(3,5-dimethoxyphenyl)carbamate (10.2 g) in a yield of 88% (calculated from the starting 3,5-dimethoxyaniline). M.P., 64.5°–65° C.

Elementary analysis: Calcd. for $C_{10}H_{13}O_4N$: N, 6.63%; C, 56.86%; H, 6.20%. Found: N, 6.65%; C, 56.97%; H, 6.31%.

Some typical examples of the N-phenylcarbamates (I) can be prepared in the same manner as above are shown in Table 1.

TABLE 1

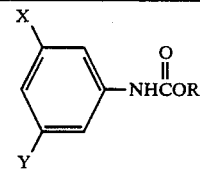

| Compound No. | X | Y | R | Physical constant |
|---|---|---|---|---|
| 1 | Cl | Cl | $CH_3$ | M.P. 116.5–117° C. |
| 2 | Cl | Cl | $C_2H_5$ | M.P. 70.5–71° C. |
| 3 | Br | Br | $CH_3$ | M.P. 131–132° C. |
| 4 | Br | Br | $C_2H_5$ | M.P. 118.5–119.5° C. |
| 5 | I | I | $CH_3$ | M.P. 158–158.5° C. |
| 6 | I | I | $C_2H_5$ | M.P. 133.5–134° C. |
| 7 | $CH_3$ | $CH_3$ | $CH_3$ | M.P. 42–43° C. |
| 8 | $CH_3$ | $CH_3$ | $C_2H_5$ | M.P. 69–70° C. |
| 9 | $C_2H_5$ | $C_2H_5$ | $CH_3$ | $n_D^{21.0}$ 1.5326 |
| 10 | $C_2H_5$ | $C_2H_5$ | $C_2H_5$ | M.P. 31–31.5° C. |
| 11 | $OCH_3$ | $OCH_3$ | $CH_3$ | M.P. 64.5–65° C. |
| 12 | $OCH_3$ | $OCH_3$ | $C_2H_5$ | $n_D^{23.5}$ 1.5418 |
| 13 | $OC_2H_5$ | $OC_2H_5$ | $CH_3$ | $n_D^{25.5}$ 1.5336 |
| 14 | $OC_2H_5$ | $OC_2H_5$ | $C_2H_5$ | $n_D^{25}$ 1.5191 |
| 15 | $OC_3H_7(i)$ | $OC_3H_7(i)$ | $CH_3$ | $n_D^{22.0}$ 1.5215 |
| 16 | $OC_3H_7(i)$ | $OC_3H_7(i)$ | $C_2H_5$ | M.P. 81.5–82° C. |
| 17 | Cl | Br | $CH_3$ | M.P. 102–102.5° C. |
| 18 | Cl | Br | $C_2H_5$ | M.P. 84–85° C. |
| 19 | Cl | $CH_3$ | $CH_3$ | M.P. 35–36° C. |
| 20 | Cl | $CH_3$ | $C_2H_5$ | M.P. 78–80° C. |

On the actual application as fungicides, the N-phenylcarbamate compounds (I) may be used by themselves only, but usually they are used in the form of an appropriate agricultural preparation such as dusts, wettable powders, oil sprays, emulsifiable concentrates, tablets, granules, fine granules, aerosols and flowables.

These preparations can be formulated in a per se conventional manner by mixing at least one of the N-phenylcarbamate compounds (I) with an appropriate solid or liquid carrier(s) or diluent(s) with or without an appropriate adjuvant(s) (e.g. surfactants, adherents, dispersants, stabilizers) for improving the dispersibility and other properties of the active ingredient at use.

Examples of the solid carriers or diluents are botanical materials (e.g. flour, tobacco stalk powder, soybean powder, walnut shell powder, wooden powder, saw dust, bran, bark powder, cellulose powder, vegetable extract residue), fibrous materials (e.g. paper, corrugated cardboard, oil rags), synthesized plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers are water, alcohols (e.g. methanol, ethanol), ketones (e.g. acetone, methyl ethyl ketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphates mixture), TCP (tricresyl phosphate), tolu oil, epoxydized oil, various surfactants, various fatty acids and their esters, etc.

The foregoing preparations generally contain at least one of the N-phenylcarbamate compounds (I) in a concentration of about 1 to 95% by weight, preferably of about 5 to 80% by weight.

When only the drug-resistant strains of phytopathogenic fungi are present, the N-phenylcarbamate compounds (I) may be used alone. When, however, the drugsensitive strains are present together with the drug-resistant strains, their use alternatively with benzimidazole thiophanate fungicides and/or cyclic imide fungicides or their use in combination with benzimidazole thiophanate fungicides and/or cyclic imide fungicides is favorable. On such alternative or combined use, the active ingredients may be employed by themselves alone or in conventional preparation forms including appropriate carriers or diluents as explained above. In case of the said combined used, the weight proportion of the N-phenylcarbamate compound (I) and the benzimidazole thiophanate fungicide and/or the cyclic imide fungicide may be from about 1:0.1 to 1:10.0. The concentration of these active ingredients in agricultural preparations as conventionally formulated may be usually from about 1.0 to 95.0% by weight, preferably from about 2.0 to 80.0% by weight.

Without any limitation, some typical examples of the benzimidazole thiophanate fungicides and the cyclic imide fungicides as preferably employed are shown in Table 2.

TABLE 2

| Compound No. | Structure | Name |
|---|---|---|
| A | (benzimidazole)-NHCOOCH₃, N-CONHC₄H₉(n) | Methyl-1-(butylcarbamoyl)benzimidazol-2-yl-carbamate |
| B | 2-(4-thiazolyl) benzimidazole structure | 2-(4-Thiazolyl)-benzimidazole |
| C | benzimidazole-NHCOOCH₃ | Methylbenzimidazole-2-ylcarbamate |
| D | 2-(2-furyl)benzimidazole structure | 2-(2-Furyl)benzimidazole |
| E | benzene with two NHCNHCOOCH₃ (C=S) groups | 1,2-Bis(3-methoxycarbonyl-2-thioureido)benzene |
| F | benzene with two NHCNHCOOC₂H₅ (C=S) groups | 1,2-Bis(3-Ethoxycarbonyl-2-thioureido)benzene |
| G | NHCHCOOCH₃ and NHP(=S)(OCH₃)—S—CH₃ substituted benzene | 2-(O,S—Dimethylphosphorylamino)-1-(3′-methoxycarbonyl-2′-thioureido)-benzene |
| H | NHCNHCOOCH₃ (C=S) and NHP(=S)(OCH₃)₂ substituted benzene | 2-(O,O—Dimethylthiophosphorylamino-1-(3′-methylcarbonyl-2′-thioureido)-benzene |
| I | 3,5-dichlorophenyl-1,2-dimethylcyclopropane-1,2-dicarboximide structure | N—(3′,5′-Dichlorophenyl)-1,2-dimethylcyclopropane-1,2-dicarboximide |
| J | 3,5-dichlorophenyl imidazolidine-2,4-dione with N—C(=O)—NHCH(CH₃)₂ | 3-(3′,5′-Dichlorophenyl)-1-isopropylcarbonylimidazolidin-2,4-dione |
| K | 3,5-dichlorophenyl oxazolidin-2,4-dione with CH=CH₂ and CH₃ | 3-(3′,5′-Dichlorophenyl)-5-methyl-5-vinyloxazolidin-2,4-dione |
| L | 3,5-dichlorophenyl oxazolidine with COOC₂H₅ and CH₃ | Ethyl (RS)-3-(3′,5′-Dichlorophenyl)-5-methyl-2,4-dioxo-oxazolidine-5-carboxylate |

A suitable amount of the preparations to be applied may be generally such as containing about 10 to 100 grams of the N-phenylcarbamate compound(s) (I) per 10 are, and the concentration of the active ingredient(s) is preferably within a range of about 0.005 to 0.5% by weight. Since, however, the amount and concentration depend upon the preparation forms, application times, application methods, application sites, diseases and crops, they may be properly increased or decreased irrespective of the aforesaid ranges.

Besides, the N-phenylcarbamate compound(s) (I) may be used in admixture with other fungicides (except benzimidazole thiophanate fungicides and cyclic imide fungicides), herbicides, insecticides, miticides, fertilizers, etc.

Some practical embodiments of the fungicidal composition according to the invention are illustratively shown in the following Examples wherein % and part(s) are by weight.

PREPARATION EXAMPLE 1

Two parts of Compound No. 4, 88 parts of clay and 10 parts of talc were thoroughly pulverized and mixed together to obtain a dust preparation containing 2% of the active ingredient.

PREPARATION EXAMPLE 2

Thirty parts of Compound No. 2, 45 parts of diatomaceous earth, 20 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredient.

PREPARATION EXAMPLE 3

Fifty parts of Compound No. 1, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredient.

PREPARATION EXAMPLE 4

Ten parts of Compound No. 3, 80 parts of cyclohexanone and 10 parts of polyoxyethylene alkylaryl ether as an emulsifier were mixed together to obtain an emulsifiable concentrate preparation containing 10% of the active ingredient.

PREPARATION EXAMPLE 5

One part of Compound No. 1, 1 part of Compound No. C, 88 parts of clay and 10 parts of talc were thoroughly pulverized and mixed together to obtain a dust preparation containing 2% of the active ingredients.

PREPARATION EXAMPLE 6

Two parts of Compound No. 4, 2 parts of Compound No. E, 86 parts of clay and 10 parts of talc were thoroughly pulverized and mixed together to obtain a dust preparation containing 4% of the active ingredients.

PREPARATION EXAMPLE 7

One part of Compound No. 13, 2 parts of Compound No. I, 87 parts of clay and 10 parts of talc were thoroughly pulverized and mixed together to obtain a dust preparation containing 3% of the active ingredients.

PREPARATION EXAMPLE 8

Twenty parts of Compound No. 9, 10 parts of Compound No. G, 45 parts of diatomaceous earth, 20 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredients.

PREPARATION EXAMPLE 9

Ten parts of Compound No. 6, 40 parts of Compound No. A, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredients.

PREPARATION EXAMPLE 10

Twenty-five parts of Compound No. 2, 50 parts of Compound No. F, 18 parts of diatomaceous earth 3.5 parts of calcium alkylbenzenesulfonate as a wetting agent and 3.5 parts of calcium ligninsulfonate as a dispersing agent were mixed while being powdered to obtain a wettable powder preparation containing 75% of the active ingredients.

PREPARATION EXAMPLE 11

Twenty parts of Compound No. 14, 30 parts of Compound No. J, 40 parts of powdery sucrose, 5 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredients.

PREPARATION EXAMPLE 12

Thirty parts of Compound No. 13, 20 parts of Compound No. H, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredients.

PREPARATION EXAMPLE 13

Fifty parts of Compound No. 20, 25 parts of Compound No. K, 18 parts of diatomaceous earth, 3.5 parts of calcium alkylbenzenesulfonate as a wetting agent and 3.5 parts of calcium ligninsulfonate as a dispersing agent were mixed while being powdered to obtain a wettable powder preparation containing 75% of the active ingredients.

PREPARATION EXAMPLE 14

One part of Compound No. 18, 1 part of Compound No. G, 88 parts of clay and 10 parts of talc were thoroughly pulverized and mixed together to obtain a dust preparation containing 2% of the active ingredients.

PREPARATION EXAMPLE 15

A ½ part of Compound No. 7, 0.5 part of Compound No. B, 89 parts of clay and 10 parts of talc were thoroughly pulverized and mixed together to obtain a dust preparation containing 1% of the active ingredients.

PREPARATION EXAMPLE 16

Two parts of Compound No. 13, 1 part of Compound No. A, 87 parts of clay and 10 parts of talc were thoroughly pulverized and mixed together to obtain a dust preparation containing 3% of the active ingredients.

PREPARATION EXAMPLE 17

Twenty parts of Compound No. 3, 10 parts of Compound No. D, 40 parts of powdery sucrose, 5 parts of white carbon, 3 parts of sodium laurylsulfonate as a wetting agent and 2 parts of calcium ligninsulfonate as a dispersing agent were mixed while being powdered to obtain a wettable powder preparation containing 30% of the active ingredients.

PREPARATION EXAMPLE 18

Thirty parts of Compound No. 10, 20 parts of Compound No. K, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredients.

PREPARATION EXAMPLE 19

Fifty parts of Compound No. 8, 25 parts of Compound No. I, 18 parts of diatomaceous earth, 3.5 parts of calcium alkylbenzenesulfonate as a wetting agent and 3.5 parts of calcium ligninsulfonate as a dispersing agent were mixed while being powdered to obtain a wettable powder preparation containing 75% of the active ingredients.

The following Examples show some typical test data indicating the excellent fungicidal activity of the N-phenylcarbamates (I). The compounds used for comparison are as follows:

| Compound | Remarks |
|---|---|
| Control (a) — 3-Cl-C$_6$H$_4$-NHCOCH$_3$ | Synthesized for comparison |
| Control (b) — 4-Cl-C$_6$H$_4$-NHCOCH$_3$ | Synthesized for comparison |
| Control (c) — 2-Cl-C$_6$H$_4$-NHCOCH$_3$ | Synthesized for comparison |
| Control (d) — 3-Cl-C$_6$H$_4$-NHCOC$_2$H$_5$ | Synthesized for comparison |
| Control (e) — 4-Cl-C$_6$H$_4$-NHCOC$_2$H$_5$ | Synthesized for comparison |
| Control (f) — 2-Cl-C$_6$H$_4$-NHCOC$_2$H$_5$ | Synthesized for comparison |
| Control (g) — 3-Br-C$_6$H$_4$-NHCOCH$_3$ | Synthesized for comparison |
| Control (h) — 3-Br-C$_6$H$_4$-NHCOC$_2$H$_5$ | Synthesized for comparison |
| Control (i) — 3,5-Cl$_2$-C$_6$H$_3$-NHCOCH(CH$_3$)$_2$ | Agricultural Biological Chemistry, 35, 1707–1719 (1971) |
| Control (j) — 3,5-Cl$_2$-C$_6$H$_3$-NHCOCH$_2$CH=CH$_2$ | Agricultural Biological Chemistry, 35, 1707–1719 (1971) |
| Control (k) — 3,5-Cl$_2$-C$_6$H$_3$-NHCOCH$_2$CH$_2$Cl | Agricultural Biological Chemistry, 35, 1707–1719 (1971) |
| Control (l) — 3,5-Cl$_2$-C$_6$H$_3$-NHCOCH$_2$CN | Agricultural Biological Chemistry, 35, 1707–1719 (1971) |
| Swep — 3,4-Cl$_2$-C$_6$H$_3$-NHCOCH$_3$ | Commercially available herbicide |
| Chlorpropham | |

-continued

| Compound | Remarks |
|---|---|
| [structure: 3-Cl-C6H4-NHCOCH(CH3)2]<br>Barban | Commercially available herbicide |
| [structure: 3-Cl-C6H4-NHCOCH2C≡CCH2Cl]<br>CEPC | Commercially available herbicide |
| [structure: 3-Cl-C6H4-NHCOCH2CH2Cl]<br>Propham | Commercially available herbicide |
| [structure: C6H5-NHCOCH(CH3)2]<br>Chlorbufam | Commercially available herbicide |
| [structure: 3-Cl-C6H4-NHCOCH(C≡CH)CH3]<br>Benomyl | Commercially available herbicide |
| [benzimidazole structure with CONHC4H9 and NHCOOCH3]<br>Thiophanate-methyl | Commercially available fungicide |
| [structure: phenyl with two NHC(S)NHCOOCH3 groups]<br>Carbendazim | Commercially available fungicide |
| [benzimidazole-NHCOOCH3]<br>Thiabendazole | Commercially available fungicide |
| [benzimidazole with thiazole substituent] | Commercially available fungicide |

TEST EXAMPLE 1

Protective activity test on powdery mildew of cucumber (Sphaerotheca fuliginea):

A flower pot of 90 ml volume was filled with sandy soil, and seeds of cucumber (var: Sagami-hanjiro) were sowed therein. Cultivation was carried out in a greenhouse for 8 days. Onto the resulting seedlings having cotyledons the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Sphaerotheca fuliginea* by spraying and further cultivated in the greenhouse. Ten days thereafter, the infectious state of the plants was observed. The degree of damage was determined in the following manner, and the results are shown in Table 3.

The leaves examined were measured for a percentage of infected area and classified into the corresponding disease indices, 0, 0.5, 1, 2, 4:

| Disease index | Percentage of infected area |
|---|---|
| 0 | No infection |
| 0.5 | Infected area of less than 5% |
| 1 | Infected area of less than 20% |
| 2 | Infected area of less than 50% |
| 4 | Infected area of not less than 50% |

The disease severity was calculated according to the following equation:

$$\text{Disease severity (\%)} = \frac{(\text{Disease index}) \times (\text{Number of leaves})}{4 \times (\text{Total number of leaves examined})} \times 100$$

The prevention value was calculated according to the following equation:

$$\text{Prevention value (\%)} = 100 - \frac{(\text{Disease severity in treated plot})}{(\text{Disease severity in untreated plot})} \times 100$$

TABLE 3

| Compound No. | Concentration of active ingredient (ppm) | Prevention value when inoculated with drug-resistant strain (%) | Prevention value when inoculated with drug-sensitive strain (%) |
|---|---|---|---|
| 1 | 200 | 100 | 0 |
| 2 | 200 | 100 | 0 |
| 3 | 200 | 100 | 0 |
| 4 | 200 | 100 | 0 |
| 5 | 200 | 100 | 0 |
| 6 | 200 | 100 | 0 |
| 7 | 200 | 100 | 0 |
| 8 | 200 | 100 | 0 |
| 9 | 200 | 98 | 0 |
| 10 | 200 | 100 | 0 |
| 11 | 200 | 100 | 0 |
| 12 | 200 | 95 | 0 |
| 13 | 200 | 98 | 0 |
| 14 | 200 | 100 | 0 |
| 15 | 200 | 95 | 0 |
| 16 | 200 | 100 | 0 |
| 17 | 200 | 100 | 0 |
| 18 | 200 | 100 | 0 |
| 19 | 200 | 100 | 0 |
| 20 | 200 | 100 | 0 |
| Control (a) | 200 | 0 | 0 |
| Control (b) | 200 | 0 | 0 |

TABLE 3-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| Control (c) | 200 | 0 | 0 |
| Control (d) | 200 | 0 | 0 |
| Control (e) | 200 | 0 | 0 |
| Control (f) | 200 | 0 | 0 |
| Control (g) | 200 | 0 | 0 |
| Control (h) | 200 | 0 | 0 |
| Control (i) | 200 | 0 | 0 |
| Control (j) | 200 | 0 | 0 |
| Control (k) | 200 | 0 | 0 |
| Control (l) | 200 | 0 | 0 |
| Swep | 200 | 0 | 0 |
| Chlorpropham | 200 | 0 | 0 |
| Barban | 200 | 25 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 3, the N-phenylcarbamates (I) of the invention show an excellent preventive effect on the drug-resistant strain but do not show any preventive effect on the drug-sensitive strain. To the contrary, commercially available known fungicides such as Benomyl, Thiophanate-methyl and Carbendazim show a notable controlling effect on the drug-sensitive strain but not on the drug-resistant strain. Other compounds structurally similar to the N-phenylcarbamates (I) do not show any fungicidal activity on the drug-sensitive strain and the drug-resistant strain.

TEST EXAMPLE 2

Preventive effect on cercospora leaf spot of sugar beet (Cercospora beticola):

A flower pot of 90 ml volume was filled with sandy soil, and seeds of sugar beet (var: Detroit dark red) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora beticola* by spraying. The pot was covered with a polyvinyl chloride sheet to make a condition of high humidity, and cultivation was continued in the greenhouse for 10 days. The degree of damage was determined in the same manner as in Test Example 1, and the results are shown in Table 4.

TABLE 4

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 100 | 0 |
|  | 50 | 100 | 0 |
| 2 | 200 | 100 | 0 |
|  | 50 | 98 | 0 |
| 3 | 200 | 100 | 0 |
|  | 50 | 100 | 0 |
| 4 | 200 | 100 | 0 |
|  | 50 | 94 | 0 |
| 5 | 200 | 100 | 0 |
| 6 | 200 | 100 | 0 |
| 7 | 200 | 100 | 0 |
| 8 | 200 | 100 | 0 |
| 9 | 200 | 100 | 0 |
| 10 | 200 | 100 | 0 |
| 11 | 200 | 100 | 0 |
| 12 | 200 | 98 | 0 |
| 13 | 200 | 100 | 0 |
| 14 | 200 | 100 | 0 |
| 15 | 200 | 100 | 0 |
| 16 | 200 | 95 | 0 |
| 17 | 200 | 100 | 0 |
| 18 | 200 | 100 | 0 |
| 19 | 200 | 100 | 0 |
| 20 | 200 | 100 | 0 |
| Control (a) | 200 | 0 | 0 |
|  | 50 | 0 | 0 |
| Control (b) | 200 | 0 | 0 |
|  | 50 | 0 | 0 |
| Control (c) | 200 | 0 | 0 |
|  | 50 | 0 | 0 |
| Control (d) | 200 | 0 | 0 |
|  | 50 | 0 | 0 |
| Control (e) | 200 | 0 | 0 |
|  | 50 | 0 | 0 |
| Control (f) | 200 | 0 | 0 |
|  | 50 | 0 | 0 |
| Control (g) | 200 | 0 | 0 |
|  | 50 | 0 | 0 |
| Control (h) | 200 | 0 | 0 |
|  | 50 | 0 | 0 |
| Control (i) | 200 | 0 | 0 |
|  | 50 | 0 | 0 |
| Control (j) | 200 | 0 | 0 |
|  | 50 | 0 | 0 |
| Control (k) | 200 | 0 | 0 |
|  | 50 | 0 | 0 |
| Control (l) | 200 | 0 | 0 |
|  | 50 | 0 | 0 |
| Swep | 200 | 0 | 0 |
|  | 50 | 0 | 0 |
| Chlorpropham | 200 | 0 | 0 |
|  | 50 | 0 | 0 |
| Barban | 200 | 34 | 0 |
|  | 50 | 0 | 0 |
| CEPC | 200 | 0 | 0 |
|  | 50 | 0 | 0 |
| Propham | 200 | 0 | 0 |
|  | 50 | 0 | 0 |
| Chlorbufam | 200 | 0 | 0 |
|  | 50 | 0 | 0 |
| Benomyl | 200 | 0 | 100 |
|  | 50 | 0 | 100 |
| Thiophanate-methyl | 200 | 0 | 100 |
|  | 50 | 0 | 98 |

As understood from the results shown in Table 4, the N-phenylcarbamates (I) of the invention show an excellent preventive effect on the drug-resistant strain but do not show any preventive effect on the drug-sensitive strain. To the contrary, commercially available known fungicides such as Benomyl and Thiophanate-methyl show a notable controlling effect on the drug-sensitive strain but not on the drug-resistant strain. Other compounds structurally similar to the N-phenylcarbamates (I) do not show any fungicidal activity on the drug-sensitive strain and the drug-resistant strain.

TEST EXAMPLE 3

Preventive effect on scab of pear (Venturia nashicola):

A plastic pot of 90 ml volume was filled with sandy soil, and seeds of pear (var: Chojuro) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Venturia nashicola* by spraying. The resulting plants were placed at 20° C. under a condition of high humidity for 3 days and then at 20° C. under irradiation with a ultraviolet lamp for 20 days. The degree of damage was determined in the same manner as in Test Example 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 100 | 0 |
|   | 50  | 100 | 0 |
| 2 | 200 | 100 | 0 |
|   | 50  | 100 | 0 |
| 3 | 200 | 100 | 0 |
|   | 50  | 100 | 0 |
| 4 | 200 | 100 | 0 |
|   | 50  | 100 | 0 |
| 5 | 200 | 100 | 0 |
| 6 | 200 | 100 | 0 |
| 7 | 200 | 100 | 0 |
| 8 | 200 | 100 | 0 |
| 9 | 200 | 98  | 0 |
| 10 | 200 | 100 | 0 |
| 11 | 200 | 100 | 0 |
| 12 | 200 | 95  | 0 |
| 13 | 200 | 100 | 0 |
| 14 | 200 | 100 | 0 |
| 15 | 200 | 100 | 0 |
| 16 | 200 | 100 | 0 |
| 17 | 200 | 100 | 0 |
| 18 | 200 | 100 | 0 |
| 19 | 200 | 100 | 0 |
| 20 | 200 | 100 | 0 |
| Benomyl | 200 | 0 | 100 |
|         | 50  | 0 | 100 |
| Thiophanate-methyl | 200 | 0 | 100 |
|                    | 50  | 0 | 100 |

As understood from the results shown in Table 5, the N-phenylcarbamates (I) of the invention show an excellent preventive effect on the drug-resistant strain but do not show any preventive effect on the drug-sensitive strain. To the contrary, commercially available known fungicides such as Benomyl and Thiophanate-methyl show a notable controlling effect on the drug-sensitive strain but not on the drug-resistant strain.

TEST EXAMPLE 4

Preventive effect on brown leaf-spot of peanut (Cercospora arachidicola):

A plastic pot of 100 ml volume was filled with sandy soil, and seeds of peanut (var: Chiba hanryusei) were sowed therein. Cultivation was carried out in a greenhouse for 14 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora arachidicola* by spraying. The resulting plants were covered with a polyvinyl chloride sheet to make a condition of high humidity and cultivated in the greenhouse for 10 days. The degree of damage was determined in the same manner as in Test Example 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 100 | 0 |
|   | 50  | 100 | 0 |
| 2 | 200 | 100 | 0 |
|   | 50  | 100 | 0 |
| 3 | 200 | 100 | 0 |
|   | 50  | 100 | 0 |
| 4 | 200 | 100 | 0 |
|   | 50  | 100 | 0 |
| 5 | 200 | 100 | 0 |
| 6 | 200 | 100 | 0 |
| 7 | 200 | 100 | 0 |
| 8 | 200 | 100 | 0 |
| 9 | 200 | 100 | 0 |
| 10 | 200 | 100 | 0 |
| 11 | 200 | 100 | 0 |
| 12 | 200 | 100 | 0 |
| 13 | 200 | 96  | 0 |
| 14 | 200 | 100 | 0 |
| 15 | 200 | 98  | 0 |
| 16 | 200 | 100 | 0 |
| 17 | 200 | 98  | 0 |
| 18 | 200 | 100 | 0 |
| 19 | 200 | 100 | 0 |
| 20 | 200 | 100 | 0 |
| Benomyl | 200 | 0 | 100 |
|         | 50  | 0 | 100 |
| Thiophanate-methyl | 200 | 0 | 100 |
|                    | 50  | 0 | 100 |

As understood from the results shown in Table 6, the N-phenylcarbamates (I) of the invention show an excellent preventive effect on the drug-resistant strain but do not show any preventive effect on the drug-sensitive strain. To the contrary, commercially available known fungicides such as Benomyl and Thiophanate-methyl show a notable controlling effect on the drug-sensitive strain but not on the drug-resistant strain.

TEST EXAMPLE 5

Preventive effect on green mold of orange (Penicillium italicum):

Fruits of orange (var: Unshu) were washed with water and dried in the air. The fruits were immersed in a solution of the test compound prepared by diluting an emulsifiable concentrate comprising the test compound with water for 1 minute. After drying in the air, the fruits were inoculated with a spore suspension of the drug-resistant or drug-sensitive strain of *Penicillium italicum* by spraying and placed in a room of high humidity for 14 days. The degree of damage was determined in the following manner:

The fruits examined were measured for a percentage of infected area and classified into the corresponding indices, 0, 1, 2, 3, 4, 5:

| Disease index | Percentage of infected area |
| --- | --- |
| 0 | No infection |
| 1 | Infected area of less than 20% |
| 2 | Infected area of less than 40% |
| 3 | Infected area of less than 60% |
| 4 | Infected area of less than 80% |
| 5 | Infected area of not less than |

-continued

| Disease index | Percentage of infected area |
|---|---|
| | 80% |

Calculation of the degree of damage and the prevention value was made as in Test Example 1.
The results are shown in Table 7.

TABLE 7

| Compound No. | Concentration of active ingredient (ppm) | Prevention value when inoculated with drug-resistant strain (%) | Prevention value when inoculated with drug-sensitive strain (%) |
|---|---|---|---|
| 1 | 200 | 100 | 0 |
| | 50 | 100 | 0 |
| 2 | 200 | 100 | 0 |
| | 50 | 100 | 0 |
| 3 | 200 | 100 | 0 |
| | 50 | 100 | 0 |
| 4 | 200 | 100 | 0 |
| | 50 | 100 | 0 |
| 5 | 200 | 100 | 0 |
| 6 | 200 | 100 | 0 |
| 7 | 200 | 100 | 0 |
| 8 | 200 | 100 | 0 |
| 9 | 200 | 100 | 0 |
| 10 | 200 | 98 | 0 |
| 11 | 200 | 100 | 0 |
| 12 | 200 | 100 | 0 |
| 13 | 200 | 100 | 0 |
| 14 | 200 | 100 | 0 |
| 15 | 200 | 100 | 0 |
| 16 | 200 | 100 | 0 |
| 17 | 200 | 100 | 0 |
| 18 | 200 | 100 | 0 |
| 19 | 200 | 100 | 0 |
| 20 | 200 | 100 | 0 |
| Benomyl | 200 | 0 | 100 |
| | 50 | 0 | 100 |
| Thiophanate-methyl | 200 | 0 | 100 |
| | 50 | 0 | 100 |
| Thiabendazole | 200 | 0 | 100 |
| | 50 | 0 | 100 |

As understood from the results in Table 7, the N-phenylcarbamates (I) show an excellent preventive effect on the drug-resistant strain, whereas commercially available known fungicides such as Benomyl, Thiophanate-methyl and Thiabendazole show a remarkable preventive effect on the drug-sensitive strain.

TEST EXAMPLE 6

Phytotoxicity on crop plants:
Plastic pots of 150 ml volume were filled with sandy soil, and seeds of wheat (var: Norin No. 61), apple (var: Kogyoku) and peanut (var: Chiba hanryusei) were sowed therein. Cultivation was carried out in a greenhouse. Onto the resulting seedlings, the test compound formulated in emulsifiable concentrate or wettable powder and diluted with water was sprayed. After cultivation in the greenhouse for an additional 10 days, the phytotoxicity was examined on the following criteria:

| Extent | Observation |
|---|---|
| − | No abnormality |
| + | Abnormality due to phytotoxicity observed in a part of crop plants |
| ++ | Abnormality due to phytotoxicity observed in entire crop plants |
| +++ | Crop plants withered due to phyto- |

| Extent | Observation |
|---|---|
| | toxicity |

The results are shown in Table 8.

TABLE 8

| Compound No. | Concentration of active ingredient (ppm) | Phytotoxicity | | |
|---|---|---|---|---|
| | | Wheat | Apple | Peanut |
| 1 | 1000 | − | − | − |
| 2 | 1000 | − | − | − |
| 3 | 1000 | − | − | − |
| 4 | 1000 | − | − | − |
| 5 | 1000 | − | − | − |
| 6 | 1000 | − | − | − |
| 7 | 1000 | − | − | − |
| 8 | 1000 | − | − | − |
| 9 | 1000 | − | − | − |
| 10 | 1000 | − | − | − |
| 12 | 1000 | − | − | − |
| 13 | 1000 | − | − | − |
| 14 | 1000 | − | − | − |
| 15 | 1000 | − | − | − |
| 16 | 1000 | − | − | − |
| 17 | 1000 | − | − | − |
| 18 | 1000 | − | − | − |
| 19 | 1000 | − | − | − |
| 20 | 1000 | − | − | − |
| Barban | 1000 | − | ++ | ++ |
| CEPC | 1000 | − | ++ | ++ |
| Swep | 1000 | ++ | ++ | + |

As understood from the results shown in Table 8, the N-phenylcarbamates (I) of the invention produce no material phytotoxicity, while commercially available herbicides having a chemical structure similar thereto produce considerable phytotoxicity.

TEST EXAMPLE 7

Preventive effect on powdery mildew of cucumber (Sphaerotheca fuliginea):
A plastic pot of 90 ml volume was filled with sandy soil, and seeds of cucumber (var: Sagami-hanjiro) were sowed therein. Cultivation was carried out in a greenhouse for 8 days. Onto the resulting seedlings having cotyledons, the test compound(s) formulated in emulsifiable concentrate or wettable powder and diluted with water were sprayed at a rate of 10 ml per pot. Then, the seedlings were inoculated with a spore suspension of the drug-resistant and drug-sensitive strains of Sphaerotheca fuliginea by spraying. The resulting plants were cultivated in the greenhouse for 10 days. The degree of damage was determined in the same manner as in Test Example 1, and the results are shown in Table 9.

TABLE 9

| Compound No. | Concentration of active ingredient (ppm) | Prevention value (%) |
|---|---|---|
| 1 | 100 | 42 |
| 1 | 20 | 0 |
| 4 | 100 | 44 |
| 4 | 20 | 0 |
| 5 | 100 | 38 |
| 5 | 20 | 0 |
| 9 | 100 | 36 |
| 9 | 20 | 0 |
| 10 | 100 | 28 |
| 10 | 20 | 0 |
| 11 | 100 | 24 |
| 11 | 20 | 0 |
| 13 | 100 | 36 |

TABLE 9-continued

| Compound No. | Concentration of active ingredient (ppm) | Prevention value (%) |
|---|---|---|
| 13 | 20 | 0 |
| 14 | 100 | 28 |
| 14 | 20 | 0 |
| 15 | 100 | 36 |
| 15 | 20 | 0 |
| 16 | 100 | 32 |
| 16 | 20 | 0 |
| 19 | 100 | 36 |
| 19 | 20 | 0 |
| 20 | 100 | 32 |
| 20 | 20 | 0 |
| A | 100 | 45 |
| A | 20 | 12 |
| F | 100 | 43 |
| F | 20 | 8 |
| G | 100 | 42 |
| G | 20 | 8 |
| H | 100 | 40 |
| H | 20 | 5 |
| 1 + A | 20 + 20 | 100 |
| 1 + F | 20 + 20 | 100 |
| 4 + A | 20 + 20 | 100 |
| 4 + F | 20 + 20 | 100 |
| 5 + A | 20 + 20 | 100 |
| 5 + F | 20 + 20 | 100 |
| 5 + G | 20 + 20 | 100 |
| 5 + H | 20 + 20 | 100 |
| 8 + G | 20 + 20 | 100 |
| 8 + H | 20 + 20 | 100 |
| 9 + A | 20 + 20 | 100 |
| 9 + F | 20 + 20 | 100 |
| 9 + G | 20 + 20 | 100 |
| 9 + H | 20 + 20 | 100 |
| 10 + A | 20 + 20 | 100 |
| 10 + F | 20 + 20 | 100 |
| 11 + A | 20 + 20 | 100 |
| 11 + F | 20 + 20 | 100 |
| 13 + G | 20 + 20 | 100 |
| 13 + H | 20 + 20 | 100 |
| 14 + G | 20 + 20 | 100 |
| 14 + H | 20 + 20 | 100 |
| 15 + A | 20 + 20 | 100 |
| 15 + F | 20 + 20 | 100 |
| 15 + G | 20 + 20 | 100 |
| 15 + H | 20 + 20 | 100 |
| 16 + A | 20 + 20 | 100 |
| 16 + F | 20 + 20 | 100 |
| 19 + G | 20 + 20 | 100 |
| 19 + H | 20 + 20 | 100 |
| 20 + G | 20 + 20 | 100 |
| 20 + H | 20 + 20 | 100 |

As understood from the results shown in Table 9, the combined use of the N-phenylcarbamates (I) of the invention with benzimidazole thiophanate fungicides and/or cyclic imide fungicides show much more excellent preventive effect than their sole use.

TEST EXAMPLE 8

Preventive effect on gray mold of tomato (Botrytis cinerea):

Plastic pots of 90 ml volume were filled with sandy soil, and seeds of tomato (var: Fukuju No. 2) were sowed therein. Cultivation was carried out in a greenhouse for 4 weeks. Onto the resulting seedlings at the four-leaf stage, the test compound(s) formulated in emulsifiable concentrate or wettable powder and diluted with water were sprayed at a rate of 10 ml per pot. Then, the seedlings were inoculated with a spore suspension of the drug-resistant and drug-sensitive strains of Botrytis cinerea by spraying. The resulting plants were placed at 20° C. in a room of high humidity for 5 days. The degree of damage was determined in the same manner as in Test Example 1, and the results are shown in Table 10.

TABLE 10

| Compound No. | Concentration of active ingredient (ppm) | Prevention value (%) |
|---|---|---|
| 1 | 50 | 36 |
| 1 | 10 | 0 |
| 2 | 50 | 40 |
| 2 | 10 | 0 |
| 3 | 50 | 32 |
| 3 | 10 | 0 |
| 4 | 50 | 38 |
| 4 | 10 | 0 |
| 5 | 100 | 42 |
| 5 | 20 | 0 |
| 6 | 100 | 35 |
| 6 | 20 | 0 |
| 7 | 50 | 28 |
| 7 | 10 | 0 |
| 8 | 50 | 32 |
| 8 | 10 | 0 |
| 9 | 50 | 44 |
| 9 | 10 | 0 |
| 10 | 50 | 36 |
| 10 | 10 | 0 |
| 11 | 50 | 38 |
| 11 | 10 | 0 |
| 12 | 50 | 30 |
| 12 | 10 | 0 |
| 13 | 100 | 42 |
| 13 | 20 | 0 |
| 14 | 100 | 39 |
| 14 | 20 | 0 |
| 15 | 250 | 45 |
| 15 | 50 | 12 |
| 16 | 250 | 42 |
| 16 | 50 | 8 |
| 17 | 100 | 40 |
| 17 | 20 | 0 |
| 18 | 100 | 38 |
| 18 | 20 | 0 |
| 19 | 50 | 26 |
| 19 | 10 | 0 |
| 20 | 50 | 32 |
| 20 | 10 | 0 |
| I | 100 | 46 |
| I | 20 | 18 |
| J | 100 | 42 |
| J | 20 | 15 |
| K | 100 | 40 |
| K | 20 | 8 |
| L | 100 | 38 |
| L | 20 | 7 |
| 1 + I | 10 + 20 | 100 |
| 1 + J | 10 + 20 | 100 |
| 1 + K | 10 + 20 | 100 |
| 1 + L | 10 + 20 | 100 |
| 2 + I | 10 + 20 | 100 |
| 2 + K | 10 + 20 | 100 |
| 3 + I | 10 + 20 | 100 |
| 3 + L | 10 + 20 | 100 |
| 4 + I | 10 + 20 | 100 |
| 5 + I | 20 + 20 | 100 |
| 5 + J | 20 + 20 | 100 |
| 6 + I | 20 + 20 | 100 |
| 6 + K | 20 + 20 | 100 |
| 7 + I | 10 + 20 | 100 |
| 7 + J | 10 + 20 | 100 |
| 8 + I | 10 + 20 | 100 |
| 9 + I | 10 + 20 | 100 |
| 10 + I | 10 + 20 | 100 |
| 11 + I | 10 + 20 | 100 |
| 12 + I | 10 + 20 | 100 |
| 13 + I | 20 + 20 | 100 |
| 14 + I | 20 + 20 | 100 |
| 15 + I | 50 + 20 | 100 |
| 16 + I | 50 + 20 | 100 |
| 17 + I | 20 + 20 | 100 |
| 18 + I | 20 + 20 | 100 |
| 19 + I | 10 + 20 | 100 |

TABLE 10-continued

| Compound No. | Concentration of active ingredient (ppm) | Prevention value (%) |
| --- | --- | --- |
| 20 + I | 10 + 20 | 100 |

As understood from the results shown in Table 10, the combined use of the N-phenylcarbamates (I) of the invention with benzimidazole thiophanate fungicides and/or cyclic imide fungicides show much more excellent preventive effect than their sole use.

TEST EXAMPLE 9

Preventive effect on brown spot of sugar beet (Cercospora beticola):

Plastic pots of 90 ml volume were filled with sandy soil, and seeds of sugar beet (var: Detroit dark red) were sowed therein. Cultivation was carried out in a greenhouse for 2 days. Onto the resulting seedlings, the test compound(s) formulated in emulsifiable concentrate or wettable powder and diluted with water were sprayed at a rate of 10 ml per pot. Then, the seedlings were inoculated with a spore suspension of the drug-resistant and drug-sensitive strains of *Cercospora beticola* by spraying. The resulting plants were covered with a polyvinyl chloride sheet to make a condition of high humidity, and cultivation was continued in the greenhouse for 10 days. The degree of damage was determined in the same manner as in Test Example 1, and the results are shown in Table 11.

TABLE 11

| Compound No. | Concentration of active ingredient (ppm) | Prevention value (%) |
| --- | --- | --- |
| 1 | 40 | 38 |
| 1 | 10 | 0 |
| 2 | 40 | 44 |
| 2 | 10 | 0 |
| 3 | 40 | 42 |
| 3 | 10 | 2 |
| 4 | 40 | 36 |
| 4 | 10 | 0 |
| 5 | 40 | 36 |
| 5 | 10 | 0 |
| 6 | 40 | 42 |
| 6 | 10 | 0 |
| 7 | 40 | 32 |
| 7 | 10 | 0 |
| 8 | 40 | 35 |
| 8 | 10 | 0 |
| 10 | 40 | 38 |
| 10 | 10 | 0 |
| 11 | 40 | 40 |
| 11 | 10 | 0 |
| 12 | 40 | 35 |
| 12 | 10 | 0 |
| 13 | 40 | 36 |
| 13 | 10 | 0 |
| 14 | 40 | 34 |
| 14 | 10 | 0 |
| 16 | 100 | 27 |
| 16 | 20 | 0 |
| 17 | 40 | 36 |
| 17 | 10 | 0 |
| 18 | 40 | 34 |
| 18 | 10 | 0 |
| C | 20 | 26 |
| C | 5 | 0 |
| E | 40 | 42 |
| E | 10 | 0 |
| G | 40 | 46 |
| G | 10 | 8 |
| H | 20 | 27 |
| H | 5 | 0 |

TABLE 11-continued

| Compound No. | Concentration of active ingredient (ppm) | Prevention value (%) |
| --- | --- | --- |
| 1 + C | 10 + 5 | 100 |
| 1 + E | 10 + 10 | 100 |
| 1 + G | 10 + 10 | 100 |
| 1 + H | 10 + 5 | 100 |
| 2 + C | 10 + 5 | 100 |
| 2 + E | 10 + 10 | 100 |
| 2 + G | 10 + 10 | 100 |
| 2 + H | 10 + 5 | 100 |
| 3 + C | 10 + 5 | 100 |
| 3 + E | 10 + 10 | 100 |
| 3 + G | 10 + 10 | 100 |
| 3 + H | 10 + 5 | 100 |
| 4 + G | 10 + 10 | 100 |
| 4 + H | 10 + 5 | 100 |
| 5 + G | 10 + 10 | 100 |
| 5 + H | 10 + 5 | 100 |
| 6 + C | 10 + 5 | 100 |
| 6 + E | 10 + 10 | 100 |
| 6 + G | 10 + 10 | 100 |
| 6 + H | 10 + 5 | 100 |
| 7 + C | 10 + 5 | 100 |
| 7 + E | 10 + 10 | 100 |
| 7 + G | 10 + 10 | 100 |
| 7 + H | 10 + 5 | 100 |
| 8 + C | 10 + 5 | 100 |
| 8 + E | 10 + 10 | 100 |
| 10 + G | 10 + 10 | 100 |
| 10 + H | 10 + 5 | 100 |
| 11 + G | 10 + 10 | 100 |
| 11 + H | 10 + 5 | 100 |
| 12 + C | 20 + 5 | 100 |
| 12 + E | 20 + 20 | 100 |
| 12 + G | 10 + 10 | 100 |
| 12 + H | 10 + 5 | 100 |
| 13 + C | 10 + 5 | 100 |
| 13 + E | 10 + 10 | 100 |
| 14 + C | 10 + 5 | 100 |
| 14 + E | 10 + 10 | 100 |
| 16 + G | 20 + 10 | 100 |
| 16 + H | 20 + 5 | 100 |
| 17 + G | 10 + 10 | 100 |
| 17 + H | 10 + 5 | 100 |
| 18 + G | 10 + 10 | 100 |
| 18 + H | 10 + 5 | 100 |

As understood from the results shown in Table 11, the combined use of the N-phenylcarbamates (I) of the invention with benzimidazole thiophanate fungicides and/or cyclic imide fungicides show much more excellent preventive effect than their sole use.

TEST EXAMPLE 10

Preventive effect on green mold of orange (Penicillium italicum):

Fruits of orange (var: Unshu) were washed with water and dried in the air. The fruits were immersed in a solution of the test compound prepared by diluting an emulsifiable concentrate comprising the test compound with water for 1 minute. After drying in the air, the fruits were inoculated with a spore suspension of the drug-resistant and drug-sensitive strain of *Penicillium italicum* by spraying and placed in a room of high humidity for 14 days. The degree of damage was determined in the same manner as in Test Example 5. The results are shown in Table 12.

TABLE 12

| Compound No. | Concentration of active ingredient (ppm) | Prevention value (%) |
| --- | --- | --- |
| 1 | 40 | 35 |
| 1 | 10 | 0 |

TABLE 12-continued

| Compound No. | Concentration of active ingredient (ppm) | Prevention value (%) |
|---|---|---|
| 2 | 40 | 43 |
| 2 | 10 | 0 |
| 3 | 40 | 42 |
| 3 | 10 | 0 |
| 4 | 40 | 46 |
| 4 | 10 | 0 |
| 5 | 40 | 36 |
| 5 | 10 | 0 |
| 7 | 40 | 30 |
| 7 | 10 | 0 |
| B | 40 | 38 |
| B | 10 | 0 |
| D | 80 | 23 |
| D | 20 | 0 |
| H | 80 | 42 |
| H | 20 | 0 |
| 1 + B | 10 + 10 | 100 |
| 1 + D | 10 + 20 | 100 |
| 1 + H | 10 + 20 | 100 |
| 2 + B | 10 + 10 | 100 |
| 2 + D | 10 + 20 | 100 |
| 2 + H | 10 + 20 | 100 |
| 3 + B | 10 + 10 | 100 |
| 3 + D | 10 + 20 | 100 |
| 3 + H | 10 + 20 | 100 |
| 4 + B | 10 + 10 | 100 |
| 4 + D | 10 + 20 | 100 |
| 4 + H | 10 + 20 | 100 |
| 5 + B | 10 + 10 | 100 |
| 5 + D | 10 + 20 | 100 |
| 7 + B | 10 + 10 | 100 |
| 7 + D | 10 + 20 | 100 |

As understood from the results shown in Table 12, the combined use of the N-phenylcarbamates (I) of the invention with benzimidazole thiophanate fungicides and/or cyclic imide fungicides show much more excellent preventive effect than their sole use.

What is claimed is:

1. A method for controlling the growth of drug-resistant strains of fungi which comprises applying a fungicidally effective amount of a compound of the formula:

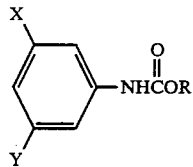

wherein X and Y, which are the same or different, are each a lower alkyl group, a lower alkoxy group or a halogen atom and R is a methyl group or an ethyl group to fungi resistant to benzimidazole fungicides including thiophanate fungicides and/or dicarboximide fungicides.

2. The method according to claim 1, wherein X and Y, which are the same or different, are each a methyl group, an ethyl group, a methoxy group, an ethoxy group, a propoxy group, a chlorine atom, a bromine atom or an iodine atom and R is a methyl group or an ethyl group.

3. The method according to claim 1, wherein said fungi are pathogenic plant fungi which have developed a resistance to benzimidazole fungicides including thiophanate selected from the group consisting of methyl 1-(butylcarbamoyl)benzimidazol-2-ylcarbamate, 2-(2-furyl)benzimidazole, 2-(4-thiazolyl)-benzimidazole, methyl benzimidazol-2-ylcarbamate, 1,2-bis(3-methoxycarbonyl-2-thioureido)benzene, 1,2-bis(3-ethoxycarbonyl-2-thioureido)benzene, 2-(O,S-dimethylphosphorylamino)-1-(3'-methoxycarbonyl-2'-thioureido)-benzene and 2-(O,O-dimethylthiophosphorylamino)-1-(3'-methoxycarbonyl-2'-thioureido)benzene and/or dicarboximide fungicides selected from the group consisting of 3-(3',5'-dichlorophenyl)-1,2-dimethylcyclopropane-1,2-dicarboximide, 3-(3',5'-dichlorophenyl)-1-isopropylcarbamoylimidazolidine-2,4-dione, 3-(3',5'-dichlorophenyl)-5-methyl-5-vinyloxazolidine-2,4-dione and ethyl(RS)-3-(3',5'-dichlorophenyl)-5-methyl-2,4-dioxooxazolidine-5-carboxylate.

4. A method for controlling the growth of drug-resistant strains of pathogenic plant fungi, which comprises:

applying to drug-resistant strains of pathogenic plant fungi resistant to benzimidazole fungicides including thiophanate and/or dicarboximide fungicides a fungicidally effective amount of a compound of the formula:

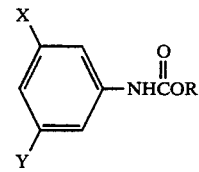

wherein X is a lower alkyl group, a lower alkoxy group, a chlorine atom, a fluorine atom, a bromine atom or an iodine atom, Y is a lower alkyl group, a lower alkoxy group, a fluorine atom, a bromine atom or an iodine atom and R is a methyl group or an ethyl group, with the proviso that X and Y are not both lower alkoxy; and an inert carrier.

5. The method according to claim 4, wherein said fungi are pathogenic plant fungi which have developed a resistance to benzimidazole fungicides including thiophanate selected from the group consisting of methyl 1-(butylcarbamoyl)-benzimidazol-2-ylcarbamate, 2-(2-furyl)benzimidazole, 2-(4-thiazolyl)benzimidazole, methyl benzimidazol-2-ylcarbamate, 1,2-bis(3-methoxycarbonyl-2-thioureido)benzene, 1,2-bis(3-ethoxycarbonyl-2-thioureido)benzene, 2-(O,S-dimethylphosphorylamino)-1-(3'-methoxycarbonyl-2'-thioureido)-benzene and 2-(O,O-dimethylthiophosphorylamino)-1-(3'-methoxycarbonyl-2'-thioureido)benzene and/or dicarboximide fungicides selected from the group consisting of 3-(3',5'-dichlorophenyl)-1,2-dimethylcyclopropane-1,2-dicarboximide, 3-(3',5'-dichlorophenyl)-1-isopropylcarbamoylimidazolidine-2,4-dione, 3-(3',5'-dichlorophenyl)-5-methyl-5-vinyloxazolidine-2,4-dione and ethyl(RS)-3-(3',5'-dichlorophenyl)-5-methyl-2,4-dioxooxazolidine-5-carboxylate.

6. A fungicidal composition comprising:

a fungicidally effective amount effective against fungi which are resistant to benzimidazole fungicides including thiophanate and dicarboximide fungicides of at least one compound of the formula:

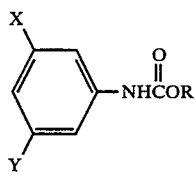

wherein X and Y, which are the same or different, are each a lower alkyl group, a lower alkoxy group or a halogen atom and R is a methyl group or an ethyl group;
a fungicidally effective amount of at least one compound selected from the group consisting of benzimidazole fungicides including thiophanate and dicarboximide fungicides; and
an inert carrier.

7. A fungicidal composition according to claim 6, wherein said benzimidazole fungicide including thiophanate is selected from the group consisting of methyl 1-(butylcarbamoyl)benzimidazol-2-ylcarbamate, 2-(2-furyl)benzimidazole, 2-(4-thiazolyl)benzimidazole, methyl benzimidazol-2-ylcarbamate, 1,2-bis(3-methoxycarbonyl-2-thioureido)benzene, 1,2-bis(3-ethoxycarbonyl-2-thioureido)benzene, 2-(O,S-dimethylphosphorylamino)-1-(3'-methoxycarbonyl-2'-thioureido)benzene, and 2-(O,O-dimethylthiophosphorylamino)-1-(3'-methoxycarbonyl-2'-thioureido)benzene and said dicarboximide fungicide is selected from the group consisting of 3-(3',5'-dichlorophenyl)-1,2-dimethylcyclopropane-1,2-dicarboximide, 3-(3-,5'-dichlorophenyl)-1-isopropylcarbamoylimidazolidine-2,4-dione, 3-(3',5'-dichlorophenyl)-5-methyl-5-vinyloxazolidine-2,4-dione and ethyl(RS)-3-(3',5'-dichlorophenyl)-5-methyl-2,4-dioxooxazolidine-5-carboxylate.

8. A fungicidal composition according to claim 6, wherein X and Y, which are the same or different, are each a methyl group, an ethyl group, a methoxy group, an ethoxy group, a propoxy group, a chlorine atom, a bromine atom or an iodine atom and R is a methyl group or an ethyl group.

9. A method for controlling fungi which comprises applying a fungicidally effective amount of the composition according to claim 6 to pathogenic plant fungi.

10. A method according to claim 9, wherein said fungi are pathogenic plant fungi which have developed a resistance to benzimidazole fungicides including thiophanate and/or dicarboximide fungicides.

* * * * *